(12) United States Patent
List et al.

(10) Patent No.: US 10,119,907 B2
(45) Date of Patent: Nov. 6, 2018

(54) ANALYTIC TEST UNIT AND TEST SYSTEM

(71) Applicant: Roche Diagnostics Operations, Inc., Indianapolis, IN (US)

(72) Inventors: Hans List, Hesseneck-Kailbach (DE); Herbert Harttig, Neustadt (DE); Simon Aigner, Heidelberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 476 days.

(21) Appl. No.: 13/762,877

(22) Filed: Feb. 8, 2013

(65) Prior Publication Data
US 2013/0150753 A1  Jun. 13, 2013

Related U.S. Application Data

(63) Continuation of application No. PCT/EP2011/063724, filed on Aug. 9, 2011.

(30) Foreign Application Priority Data

Aug. 11, 2010 (EP) .................................... 10172469

(51) Int. Cl.
*A61B 5/00* (2006.01)
*G01N 21/41* (2006.01)
(Continued)

(52) U.S. Cl.
CPC ............ *G01N 21/41* (2013.01); *A61B 5/1411* (2013.01); *A61B 5/1459* (2013.01);
(Continued)

(58) Field of Classification Search
CPC .............. A61B 5/1411; A61B 5/14532; A61B 5/15146; G01N 21/41
(Continued)

(56) References Cited

U.S. PATENT DOCUMENTS 4,866,696 A    9/1989  Longman et al.
7,052,652 B2 *  5/2006  Zanzucchi et al. ........ 422/82.05
(Continued)

FOREIGN PATENT DOCUMENTS

AU        200128299 A1   7/2001
EP        0 288 140 A2   10/1988
(Continued)

OTHER PUBLICATIONS

English translation of International Preliminary Report on Patentability, PCT/EP2011/063724, dated Feb. 12, 2013.

*Primary Examiner* — Daniel Cerioni
(74) *Attorney, Agent, or Firm* — Bose McKinney & Evans LLP

(57) ABSTRACT

This disclosure relates to an analytic test unit for use in a test device for detecting an analyte in a bodily fluid, having at least one test element with a carrier film and a reagent layer, the latter being affixed on the carrier side of the carrier film and it being possible to apply bodily fluid on said reagent layer, wherein the light-transparent carrier film can be positioned in the beam path of a photometric measuring unit for optically scanning the reagent layer. According to this disclosure, it is proposed that the carrier film has a surface, modified by a raised surface structure, for reducing reflections in the beam path of the measuring unit.

27 Claims, 3 Drawing Sheets

(51) Int. Cl.
  *A61B 5/1459* (2006.01)
  *A61B 5/1486* (2006.01)
  *A61B 5/15* (2006.01)
  *A61B 5/151* (2006.01)
  *A61B 5/157* (2006.01)
  *G01N 21/84* (2006.01)
  *G01N 31/22* (2006.01)
  *G01N 33/49* (2006.01)
  *A61B 5/145* (2006.01)

(52) U.S. Cl.
  CPC .......... *A61B 5/14865* (2013.01); *A61B 5/157* (2013.01); *A61B 5/150022* (2013.01); *A61B 5/15107* (2013.01); *A61B 5/15144* (2013.01); *A61B 5/150358* (2013.01); *A61B 5/150419* (2013.01); *A61B 5/150519* (2013.01); *A61B 5/150755* (2013.01); *G01N 21/8483* (2013.01); *G01N 31/22* (2013.01); *G01N 33/491* (2013.01); *A61B 5/14532* (2013.01); *A61B 2562/0233* (2013.01); *A61B 2562/0295* (2013.01); *A61B 2562/146* (2013.01)

(58) Field of Classification Search
  USPC ........................................................ 600/583
  See application file for complete search history.

(56) References Cited

U.S. PATENT DOCUMENTS

| | | | |
|---|---|---|---|
| 7,422,891 B2* | 9/2008 | Cunningham | ........ B01L 3/5085 356/434 |
| 8,119,069 B2 | 2/2012 | Petrich et al. | |
| 8,369,918 B2 | 2/2013 | Calasso et al. | |
| 2004/0191119 A1* | 9/2004 | Zanzucchi | ............. A61B 5/151 422/504 |
| 2005/0202567 A1 | 9/2005 | Zanzucchi et al. | |
| 2006/0173380 A1 | 8/2006 | Hoenes et al. | |
| 2007/0038149 A1 | 2/2007 | Calasso et al. | |
| 2008/0103056 A1* | 5/2008 | Lin et al. | ........................... 506/9 |
| 2008/0106742 A1 | 5/2008 | Sahiri et al. | |
| 2008/0180652 A1* | 7/2008 | Petrich | ............... G01N 21/8483 356/36 |
| 2012/0116250 A1 | 5/2012 | List | |
| 2013/0000721 A1* | 1/2013 | Nasuno | ............. H01L 31/02366 136/256 |

FOREIGN PATENT DOCUMENTS

| | | |
|---|---|---|
| EP | 2 103 256 A1 | 9/2009 |
| EP | 2 248 463 A1 | 11/2010 |
| WO | WO 2004/085995 A2 | 10/2004 |
| WO | WO 2005/006985 A2 | 1/2005 |
| WO | 2008087876 A1 | 7/2008 |

* cited by examiner

ANALYTIC TEST UNIT AND TEST SYSTEM

RELATED APPLICATIONS

This application is a continuation of PCT/EP2011/063724, filed Aug. 9, 2011, which claims priority to EP 10 172 469.8, filed Aug. 11, 2010, both of which are hereby incorporated by reference in their entireties.

BACKGROUND

The invention relates to an analytic test unit for use in a test instrument for detecting an analyte in a bodily fluid, more particularly for blood sugar tests, comprising at least one test element, which is preferably provided in a cartridge and has a carrier film and a reagent layer, which is applied to a carrier side of the carrier film and to which the bodily fluid can be applied, wherein the light-transmissive carrier film can be positioned in the beam path of a photometric measuring unit for optically scanning the reagent layer. The invention furthermore relates to a test system for processing such test units.

By way of example, such analytic test units are used in portable blood sugar measuring instruments in order to enable the user to self-determine the blood sugar level in a largely automated measurement procedure. In the process, the reagent layer is wetted on the front side with a blood sample and measured photometrically on the rear side through the carrier film. The most common method for optical evaluation consists of shining light onto the film surface at an angle of between 30° and 60° and capturing the light diffusely reflected perpendicularly to the surface by means of a photodetector. Alternatively, the positions of illumination and detection can be interchanged. The purpose of these arrangements is to keep direct reflections at the surfaces of the test structure out of the detection beam path. Such reflections result in a very high signal level at the detector but have not interacted with the test chemicals and therefore do not contain any information in respect of the analyte, which changes the test chemicals optically. Moreover, even very small changes in the angle between light incidence or light emergence and mirroring surface bring about a large signal lift in the detected light which cannot be distinguished from the modulations of the reflectance due to the analyte. Such a beam path moreover requires a relatively large installation space, which is not available when test elements are integrated into a sample collector which should obtain the sample fluid by piercing the skin, at least if many of such integrated consumables should be stored in a confined space.

Proceeding from this, this disclosure is based on the object of further improving test units and systems and enabling optimum optical measured value capture with high measuring accuracy, particularly for compact hand-held instruments.

SUMMARY

This disclosure proceeds from the idea of avoiding flat mirroring boundaries in the test structure by means of a topological surface contour. Accordingly, it is taught that the carrier film has a surface which is modified by a raised or three-dimensionally fine-structured surface structure in order to reduce reflections in the beam path of the measuring unit. Here, "fine-structured" should be understood to mean that the structure elements are smaller than the modified surface itself by a number of orders of magnitude. This renders it possible to keep bothersome reflections away from the beam path of the measuring unit by antireflective properties or light deflection. This can be achieved even in the case of surface-normal irradiation, and so particularly space-saving direct optical coupling is made possible.

The surface structure is advantageously embodied to change the refractive index of the carrier film continuously in the direction of the surface normal. Alternatively, the surface structure can form a micro-optical unit for deflecting bothersome reflections out of the beam path of the measuring unit.

A further advantageous embodiment provides for the surface structure to be arranged on the carrier side and/or on the rear side of the carrier film facing away therefrom and directed at the measuring unit.

According to a particular variant, the surface structure is arranged on the carrier side and, in particular, embodied as periodic surface relief in the style of a moth's eye structure. As a result of such a moth's eye structure, as known per se for example to provide an antireflective property to optical data carriers, it is possible to bring about a continuous change in the refractive index of the carrier film toward the reagent layer. Thus, there is no defined optical boundary between carrier film and reagent layer, and hence no reflection either.

As a result of such an embodiment, it is also possible to achieve an intrinsic refractive index adaptation if the refractive index of the reagent layer changes with time as a result of wetting with bodily fluid within the scope of the photometric measured value capture.

In order to optimize the antireflective properties, the surface structure should have a structure height in the region between 5-times and 0.2-times, preferably between 3-times and 0.7-times, preferred to be between 2-times and 1-times the wavelength of the measurement light of the measuring unit. What this also achieves is that the degree of transmission of the carrier film is increased compared to an unstructured plane surface as a result of the surface structure.

A further particularly advantageous embodiment provides for the surface structure to be formed by a prism profile on the rear side of the carrier film facing away from the carrier side. This is how it is possible to influence the measurement beam path by light refraction in order to remove bothersome reflexes.

The prism profile is advantageously formed with a profile pitch of less than 100 μm, preferably less than 50 μm, from a multiplicity of individual prisms. As a result of this, sufficient averaging over a light spot can be achieved, especially at the emergence end of an optical waveguide, and at the same time it is possible to create a sufficiently defined abutment surface for the optical coupling.

A further improvement is achieved by virtue of the fact that the prism profile is formed by a triangle profile, more particularly a saw-tooth profile, which extends in a straight line in a longitudinal direction and which is periodic transversely thereto.

The surface structures can be introduced into the carrier film as a preferably hot-stamped stamping structure formed by a stamping tool. Alternatively, it is also possible to form the aforementioned surface structures by means of a cast layer, more particularly cured in a formed fashion by means of a forming tool.

In order to further simplify the measuring procedure and the handling, it is advantageous if a collection structure for bodily fluid, which is or can be brought into fluid connection with the reagent layer, more particularly a capillary, which is arranged on a piercing element, for obtaining bodily fluid by piercing the skin, is integrated as structural unit.

The subject matter of this disclosure also relates to an analytic test system for detecting an analyte in a bodily fluid, more particularly as portable hand-held instrument for blood sugar tests, containing a photometric measuring unit and at least one test element which can be positioned in the beam path of the measuring unit and has a light-transmissive carrier film and a reagent layer, which is applied to a carrier side of the carrier film and to which the bodily fluid can be applied, wherein the carrier film has a surface which is modified by a three-dimensionally shaped surface structure in order to reduce reflections in the beam path of the measuring unit. The test units according to this disclosure with the aforementioned features can be used particularly advantageously in such a test system.

In order to develop a compact optical interface, the measuring unit may have a plurality of optical waveguides for transmitting measurement light, wherein the optical waveguides can preferably be coupled end-to-end at one end face to the rear side of the carrier film facing away from the reagent layer.

Here, parallel arrangements of illumination and detection optical waveguides have been found to be particularly suitable for building an optical interface in a very confined space (for example within only one cubic millimeter). Since, for reasons of producibility, such optical waveguides should extend in parallel, a light path is present in which reflections from all boundaries that do not lie directly on the ends of the optical waveguide could reach the detector. In order to avoid this, it is particularly advantageous if the optical waveguides are arranged parallel to one another in a common plane, at least with the end sections thereof directed at the carrier film, and if the surface structure is formed by a periodic prism profile, the profile cross section of which being perpendicular to the plane of the optical waveguides. As a result of such an arrangement, incident light is suitably refracted such that direct reflection into the reception optical waveguide is avoided. In this case, it is expedient if the lateral offset of the deflected light is greater than the diameter of the optical waveguides.

In order to increase the comfort of use for the user, it is advantageous if a multiplicity of test elements are stored in the test unit. Here, the test unit can be designed as a rotating cartridge for individual integrated sample collectors (microsampler) or as a tape cassette for successive provision of test elements on a transport tape.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

The embodiments described below are not intended to be exhaustive or to limit this disclosure to the precise forms disclosed in the following detailed description. Rather, the embodiments are chosen and described so that others skilled in the art may appreciate and understand the principles and practices of the present invention.

Figure 1:
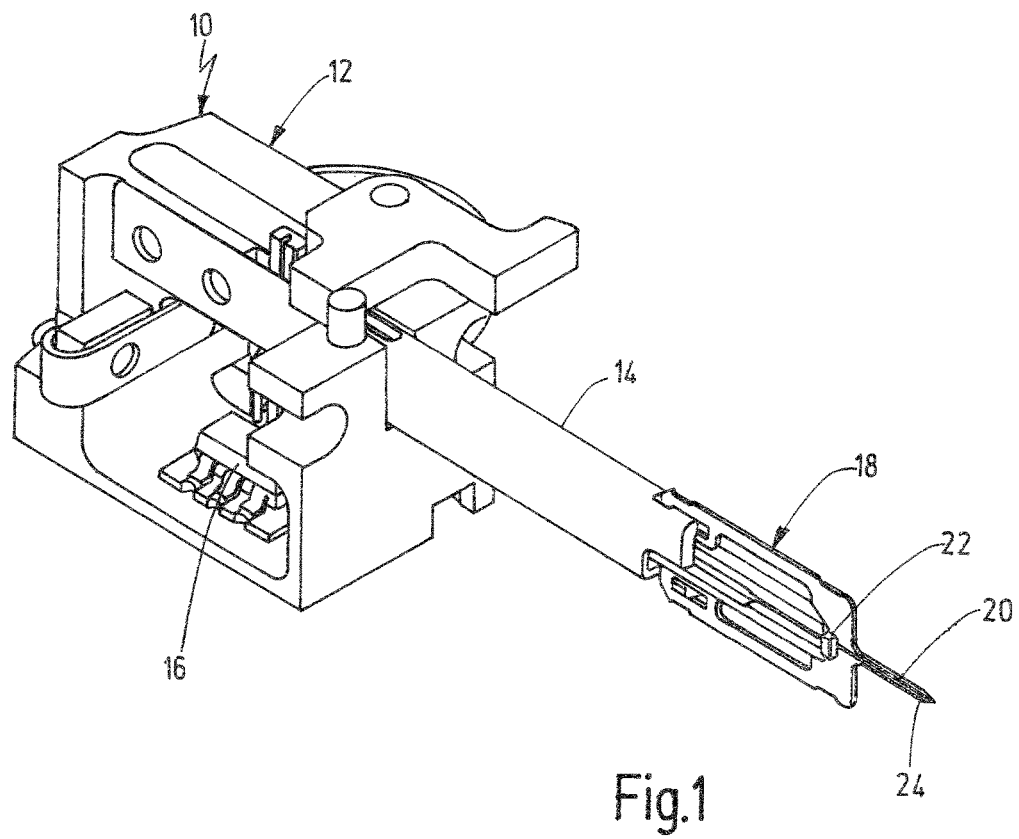
FIG. 1 shows a perspective view of an analytic blood sugar test system with a disposable test unit inserted therein.

The test system 10 illustrated in FIG. 1 comprises an instrument part 12 with an advancing and retracting piercing drive 14 and a photometric measuring unit 16 in a housing (not shown) as a portable hand-held instrument and analytic test units 18 with a piercing element 20 that can be inserted therein and an integrated test element 22 for a single test of a liquid sample, specifically for determining glucose in a blood sample. Further details of the arrangement, for example in respect of the provision of test units from a rotating cartridge, also emerge from U.S. Publication No. 2012/0116250, which is incorporated by reference herein.

Figure 2:
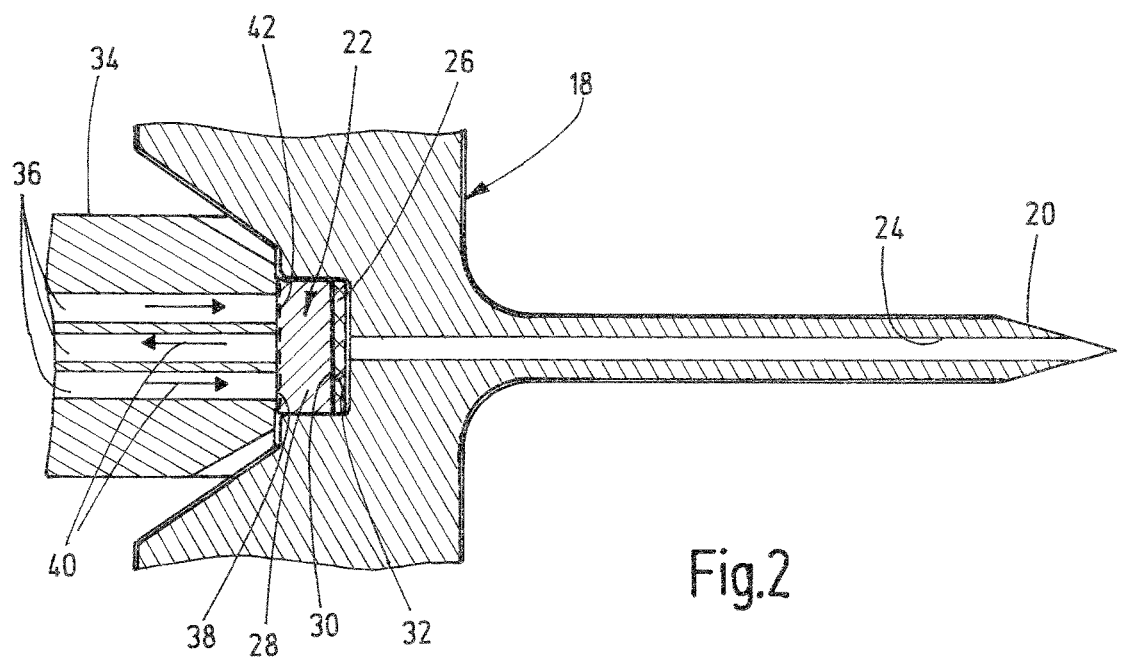
FIG. 2 shows a sectional view of the test system with an optical waveguide plunger coupled to a test element of the test unit.

As can also be seen from FIG. 2, the piercing element 20 is provided with a capillary groove 24, which, on the front side, guides the blood which was obtained when the skin was pierced, for example from a finger of a subject, to an absorbent spreading layer 26 of the integrated test element 22. The latter has a carrier film 28 and a dry-chemical reagent layer 32 enclosed under the spreading layer 26 on the carrier side 30 thereof, which reagent layer reacts with the analyte irreversibly by a color change when it is wetted by the bodily fluid. This color change can be captured (observed) from the rear side through the transparent carrier film 28. For this purpose, the measuring unit 16 has an optics adapter 34, installed as a plunger into the piercing drive 14 and containing three optical waveguides 36 extending in parallel, which with the free end faces thereof can be brought into abutment end-to-end with the rear side 38 of the carrier film 28. Here, the optical waveguides 36 are aligned in the direction of the surface normal, i.e., normal to the rear side 38 of carrier film 28. The outer optical waveguides are connected to a light transmitter, while the inner optical waveguide guides the measurement light scattered on the reagent layer 32 back to a light receiver of the measuring unit 16, as indicated in FIG. 2 by arrows as beam path 40.

In order largely to reduce bothersome reflections in the beam path 40, the carrier film 28 is on its rear side 38 and/or front side 30 provided with a surface structure 42, formed in three dimensions on a microscopic scale, which brings about a continuous refractive index profile or forms an optical unit for light deflection.

Figure 3:
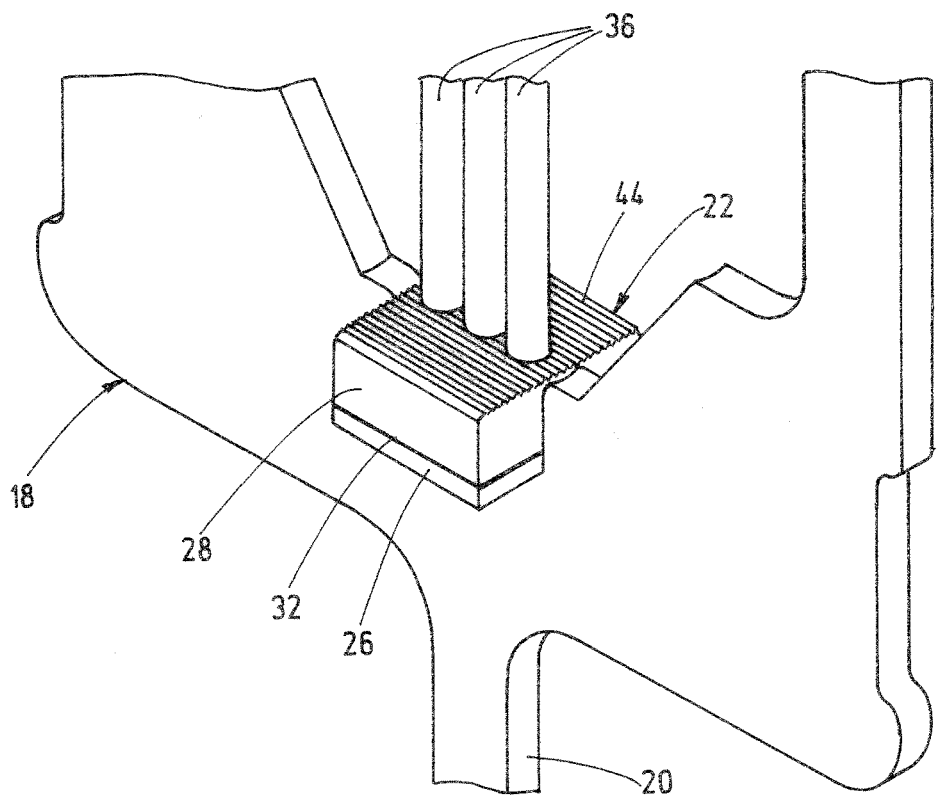
FIG. 3 shows a simplified perspective illustration of the arrangement according to FIG. 2, in which the test element has a rear-side prism structure for coupling the optical waveguides.
Figure 4:
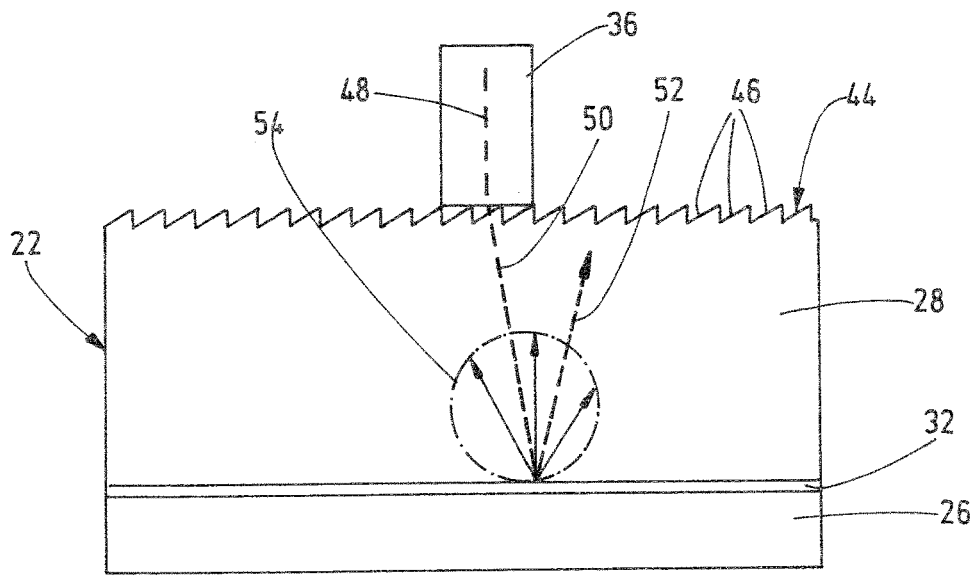
FIG. 4 shows a sectional view transverse to the plane of the optical waveguides according to FIG. 3, with a symbolized beam path.

FIGS. 2 to 4 show such an optically effective surface structure 42 in the form of a rear-side prism profile 44 on the carrier film 28. This prism profile 44 extends in a straight line, parallel to one side of the rectangular carrier film piece 28, and, transversely thereto, has a periodic saw-tooth profile 46. The profile dimensions have been selected such that irregularities in the light passage through the optical waveguides 36 over the cross section thereof are also averaged out and that a reliable abutment is ensured. In the case of an optical-waveguide diameter of 125 µm, a prism profile 44 with a profile pitch of 25 to 30 µm is very suitable. This achieves sufficient averaging over the optical-waveguide cross section while the profile structure still is sufficiently large to enable the production.

By way of example, the prism structure can be produced by cutting techniques. The formation of a cast layer on the carrier film 28 is also feasible, said layer being cured in a formed fashion by means of a suitably formed tool.

The light deflection by the prism profile 44 is illustrated in FIG. 4. The optical waveguides 36 standing substantially perpendicular to the carrier film 28 on the profile surface are arranged substantially parallel to one another in a plane which is substantially perpendicular to the illustrated profile cross-sectional area. As a result of the oblique saw-tooth profile 46, a central ray 48 emerging from the optical waveguide 36 is deflected laterally out of the plane of the optical waveguide 36 (partial beam 50) as a result of refraction. Some of this light is reflected in regular fashion at the boundary to the reagent layer 32 without interacting with the test chemical. This reflected light beam 52 emerges at the angle to the incidence normal and can therefore no longer reach the beam path of the measuring unit. The deflection angle of the prism profile 44 should be selected according to the stipulation of the acceptance angle of the optical waveguides 36 and the end-face distance thereof from the reflecting boundary.

Only that portion of the incident light 50 which reaches into the reagent layer 32 and is back-scattered from there as diffuse light lobe 54 can in part reach the measuring unit 16 via the reception optical waveguide. This measurement light therefore has interacted with the test chemical and contains information in respect of the analyte.

Figure 5:
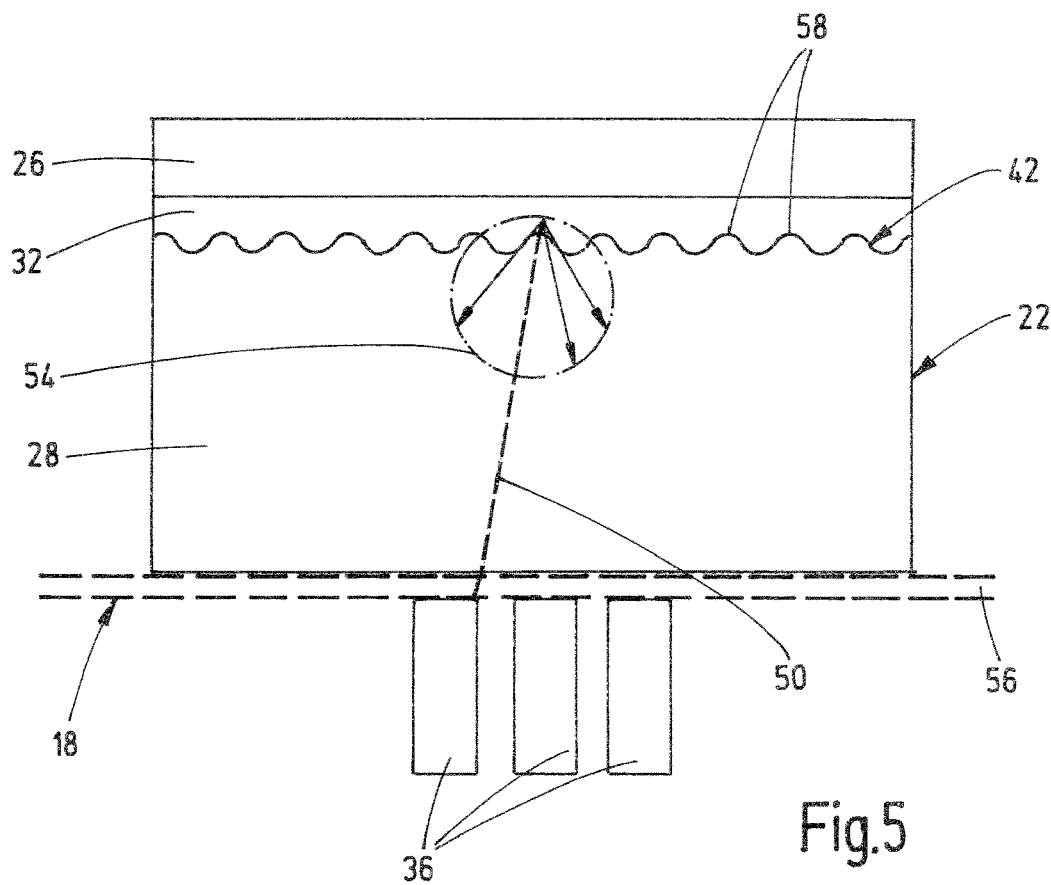
FIG. 5 shows a lateral view of a further embodiment of a test unit with a reflection-reducing moth's eye structure.
Figure 6:
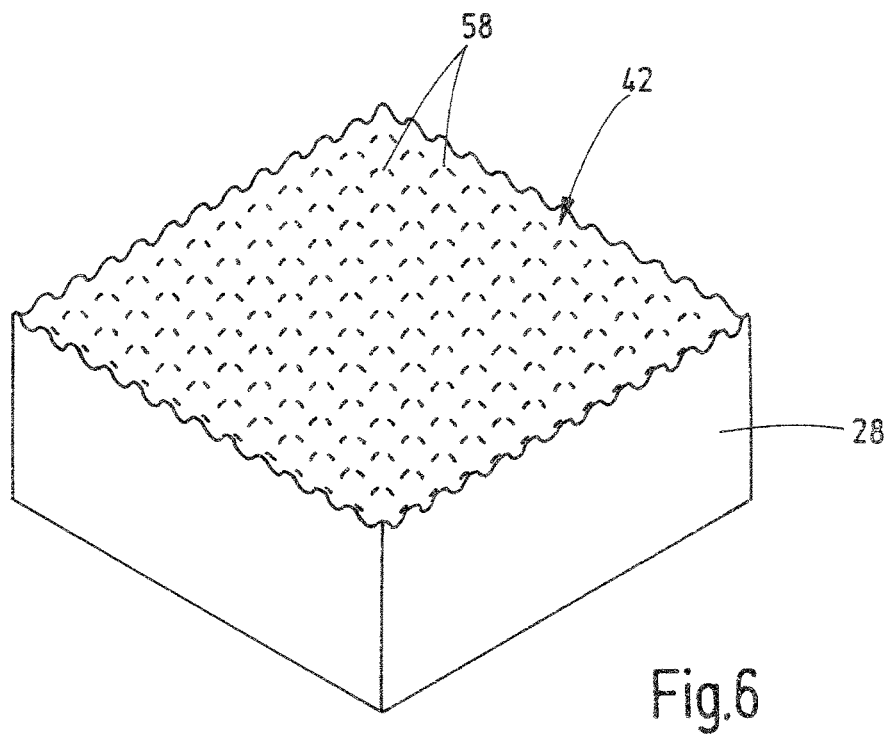
FIG. 6 shows a perspective illustration of a test carrier of the test unit according to FIG. 5.

FIGS. 5 and 6 show an exemplary embodiment of a reflection-reducing surface structure 42 which carries the reagent layer 32 on the carrier side of the block formed by the carrier film 28. Such a test element 22 can also be integrated in the piercing element 20 described above. The use in a tape cassette as test unit 18, which contains a multiplicity of test units 22 on a transparent transport tape 56 which can be wound, is also feasible.

In this case, the surface structure 42 has a periodic surface relief 58 which is formed by elevations (and complementary depressions) which are not drawn to scale and which is in the style of a so-called "moth's eye structure", as described in for example U.S. Pat. No. 4,866,696, which is hereby incorporated by reference herein. The introduction of this surface structure avoids a defined boundary and leads to a continuous change in the refractive index toward the reagent layer 32 such that an efficient antireflective property is brought about. As illustrated in FIG. 5, there is practically no mirroring at the moth's eye structure 58 (this is only shown for a marginal ray 50 of the light cone emerging from the optical waveguide 36 for reasons of simplicity), and so the degree of transmission of the carrier film 28 is increased and it is substantially only the return-scattering 54 from the reagent layer 32 which enters the reception optical waveguide as measurement light.

In the case of a narrow-band excitation, for example with a measurement wavelength of 365 nm, the elevations or depressions of the moth's eye structure 58 should have a structure height or depth in the region between 5-times and 0.2-times, preferably between 3-times and 0.7-times and preferred to be between 2-times and 1-times the measurement wavelength. The lateral structure period should also be of the order of the wavelength of the measurement light. Such nanoscale fine-structured surfaces can for example be formed on the carrier film by hot stamping by means of a stamping tool, wherein the tool surface can optionally be produced by etching.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. An analytic test unit for use in a test instrument for detecting an analyte in a bodily fluid, comprising:
   a test element having a light-transmissive carrier film;
   a reagent layer applied to the carrier film and to which bodily fluid can be applied, wherein the reagent layer includes a chemical reagent that changes color when it is wetted by the bodily fluid; and
   a spreading layer positioned adjacent the reagent layer and configured to spread the bodily fluid laterally along the regent layer;
   wherein the carrier film can be positioned in a beam path of a photometric measuring unit for optically scanning the reagent layer, the photometric measuring unit having an optical waveguide configured to transmit incident light in a direction substantially perpendicular to the carrier film, further wherein the carrier film comprises a raised surface structure configured to reduce reflections in the beam path of the measuring unit.

2. The analytic test unit of claim 1, wherein the optical waveguide is configured to be positioned substantially perpendicular to the carrier film.

3. The analytic test unit of claim 1, wherein the optical waveguide comprises at least two optical waveguides positioned substantially parallel to one another.

4. The analytic test unit of claim 3, wherein at least one the optical waveguides is configured to receive reflected light in a direction substantially perpendicular to the carrier film.

5. The analytic test unit of claim 1, wherein the optical waveguide comprises at least two optical waveguides and at least one of said waveguides is configured to receive reflected light in a direction substantially perpendicular to the carrier film.

6. The analytic test unit of claim 5, wherein each of the at least two optical waveguides is positioned substantially perpendicular to the carrier layer.

7. An analytic test unit for use in a test instrument for detecting an analyte in a bodily fluid, comprising:
   a test element having a light-transmissive carrier film;
   a reagent layer applied to the carrier film and to which bodily fluid can be applied, wherein the reagent layer includes a chemical reagent that changes color when it is wetted by the bodily fluid; and
   a spreading layer positioned adjacent the reagent layer and configured to spread the bodily fluid laterally along the reagent layer;
   wherein the carrier film can be positioned in a beam path of a photometric measuring unit for optically scanning the reagent layer, the photometric measuring unit having a plurality of optical waveguides positioned substantially parallel to one another, at least one of the waveguides configured to be positioned substantially perpendicular to the carrier film and to transmit light to the carrier film and at least another one of the waveguides configured to transmit light away from the carrier film, further wherein the carrier film comprises a raised surface structure configured to reduce reflections in the beam path of the measuring unit.

8. The analytic test element of claim 7, wherein the reagent layer is positioned between the carrier film and the spreading layer.

9. The analytic test element of claim 7, wherein the raised surface structure forms a moth's eye structure.

10. The analytic test unit of claim 7, wherein at least one of the optical waveguides is configured to transmit incident light in a direction substantially perpendicular to the carrier film.

11. The analytic test unit as claimed in claim 7, wherein the raised surface structure is arranged on a carrier side and/or on a rear side of the carrier film and faces away from the reagent layer and can be directed at the measuring unit.

12. The analytic test unit as claimed in claim 7, wherein the raised surface structure is arranged on a carrier side of the carrier film.

13. The analytic test unit as claimed in claim 7, wherein the raised surface structure has a structure height in the range between 5-times and 0.2-times the wavelength of the measurement light of the measuring unit.

14. The analytic test unit as claimed in claim 7, wherein the raised surface structure has a structure height in the range between 3-times and 0.7-times the wavelength of the measurement light of the measuring unit.

15. The analytic test unit as claimed in claim 7, wherein the raised surface structure has a structure height in the range between 2-times and 1-times the wavelength of the measurement light of the measuring unit.

16. The analytic test unit as claimed in claim 7, wherein the transmission factor of the carrier film is increased compared to an unstructured plane surface as a result of the raised surface structure.

17. The analytic test unit as claimed in claim 7, wherein the raised surface structure is formed by a prism profile on a rear side of the carrier film facing away from a carrier side.

18. The analytic test unit as claimed in claim 17, wherein the prism profile has a profile pitch of less than 100 μm from a multiplicity of individual prisms.

19. The analytic test unit as claimed in claim 17, wherein the prism profile has a profile pitch of less than 50 μm from a multiplicity of individual prisms.

20. The analytic test unit as claimed in claim 17, wherein the prism profile comprises a triangle profile which extends in a straight line in a longitudinal direction and which is periodic transversely thereto.

21. The analytic test unit as claimed in claim 20, wherein the prism profile comprises a saw-tooth profile.

22. The analytic test unit as claimed in claim 7, wherein the surface structure is stamped.

23. The analytic test unit as claimed in claim 7, wherein the surface structure is cast.

24. The analytic test unit as claimed in claim 7, further comprising a collection structure for bodily fluid which can be brought into fluid connection with the reagent layer arranged on a piercing element for obtaining bodily fluid by piercing the skin.

25. A hand-held analytic test system for detecting an analyte in a bodily fluid, comprising a photometric measuring unit and an analytic test unit according to claim 7.

26. The analytic test system as claimed in claim 25, wherein the measuring unit has a plurality of optical waveguides for transmitting measurement light and the optical waveguides are coupled end-to-end at one end face to a rear side of the carrier film facing away from the reagent layer.

27. The analytic test system as claimed in claim 26, wherein the optical waveguides are arranged parallel to one another in a common plane, with the end sections thereof directed at the carrier film.

* * * * *